United States Patent
Lewis et al.

(10) Patent No.: US 9,487,817 B2
(45) Date of Patent: Nov. 8, 2016

(54) SYSTEMS AND METHODS FOR FEEDSTOCK QUALITY ASSESSMENT

(75) Inventors: Stephen M. Lewis, Sioux Falls, SD (US); Neelakantam V. Narendranath, Sioux Falls, SD (US)

(73) Assignee: POET Research, Inc., Sioux Falls, SD (US)

( * ) Notice: Subject to any disclaimer, the term of this patent is extended or adjusted under 35 U.S.C. 154(b) by 62 days.

(21) Appl. No.: 13/993,056

(22) PCT Filed: Dec. 8, 2011

(86) PCT No.: PCT/US2011/063963
§ 371 (c)(1),
(2), (4) Date: Sep. 5, 2013

(87) PCT Pub. No.: WO2012/078885
PCT Pub. Date: Jun. 14, 2012

(65) Prior Publication Data
US 2013/0337483 A1    Dec. 19, 2013

Related U.S. Application Data

(60) Provisional application No. 61/421,454, filed on Dec. 9, 2010.

(51) Int. Cl.
*C12Q 1/44* (2006.01)
*G01N 33/10* (2006.01)
(52) U.S. Cl.
CPC ............. *C12Q 1/44* (2013.01); *G01N 33/10* (2013.01); *G01N 2333/415* (2013.01)
(58) Field of Classification Search
None
See application file for complete search history.

(56) References Cited

U.S. PATENT DOCUMENTS

| 2010/0240082 A1 | 9/2010 | Moser et al. |
| 2013/0337483 A1 | 12/2013 | Lewis |

FOREIGN PATENT DOCUMENTS

| EP | 2 649 195 | 12/2015 |
| WO | 2012-078885 | 6/2012 |

OTHER PUBLICATIONS

Megazyme, Alpha-Amylase Assay Procedure for the Measurement of Cereal and Microbial Alpha-Amylases, (1998), Available online at: secure.megazyme.com/files/Booklet/T-AMZI3G-200T_9807_DATA.pdf.*

(Continued)

*Primary Examiner* — Karen Cochrane Carlson
*Assistant Examiner* — Jennifer M. H. Tichy
(74) *Attorney, Agent, or Firm* — Amin, Turocy & Watson, LLP (57) ABSTRACT

Assessing quality of feedstock is provided and may be useful for determining quality of feed (such as corn kernels). The assessment determines endogenous enzyme activity within the feedstock, which correlates with total ethanol yields in raw starch hydrolysis (non-cooked) systems. In some embodiments, a sample containing flour (ground feedstock) is provided. In some cases, flour is diluted in water and buffered with a phosphate buffered solution. The buffered flour solution is contacted with a molecule, or fluorescent dye, such as fluorescein diacetate and/or difluorofluorescein that is altered by enzymatic (esterase) activity in a detectable fashion. Enzyme activity may be facilitated using an incubator. The detectible alteration may be measured using a fluorometer. In some embodiments, two incubations and fluorescence measurements can be performed. By subtracting the difference between the measured fluorescence, a fluorescence index may be found, which correlates with the endogenous enzyme activity in the feedstock sample.

18 Claims, 11 Drawing Sheets

(56) References Cited

OTHER PUBLICATIONS

Steward et al., A new methodology for plant cell viability assessment using intracellular esterase activity, Plant Cell Reports, 19, (1999), pp. 171-176.*

Wikipedia, Fluorescein diacetate hydrolysis, Accessed Mar. 8, 2015, Online at: en.wikipedia.org/wiki/Fluorescein_diacetate_hydrolysis.*

Lauriston, Gelatinization Temperatures for Adjunction, Posted Jul. 9, 1996, Available online at: hbd.org/brewery/library/GelTemps_RL0796.html.*

International Search Report and Written Opinion dated Aug. 17, 2002 for International Application No. PCT/US2011/063963, 14 pages.

Megazyme. "Amylazyme—Alpha-Amylase—Assay Procedure—T-AMZ200 06/07 for the Measurement of Cereal and Microbial Alpha-Amylases" Megazyme International Ireland, 2007, published online at [http://www.megazyme.com/downloadslen/data/T-AMZ200.pdf], retrieved 2012, 20 pages.

Carre, et al., "Relationships between digestibilities of food components and characteristics of wheats (*Triticum aestivum*) introduced as the only cereal source in a broiler chicken diet", British Poultry Science, vol. 43, No. 3, Jul. 2002, pp. 404-415, XP009157338, ISSN: 0007-1668, abstract p. 406, col. 2, para 3.

McLean, et al. "A Novel Method for Quantitation of Active Yeast Cells", Technical Report 2:1-5, Mar. 2001, published online at [http://genprime.com/downloads/EasyCountTechPaper.pdf], retrieved Jun. 10, 2010, 5 pages.

European Office Action dated Mar. 28, 2014 for European Application No. 11808738.6-1404, 4 pages.

Office Action for Canadian Patent Application No. 2,820,889 dated Apr. 28, 2016, 3 pages.

* cited by examiner

Example Fluorescence Measurements

| Sample | Fluorescence at 1 minute | Fluorescence at 3 minute | Fluorescence Index (Δ) |
|---|---|---|---|
| Blank | 648.4 | 691.9 | 42.5 |
| Corn flour (Regular) | 4192 | 8406 | 4214 |
| Corn flour (autoclaved) | 885.7 | 968.4 | 82.7 |

FIG. 14

Relationship Between Fluorescence Index (Corn Quality) and Fermentability

| Sample | Fluorescence Index | Ethanol (% v/v) | Glycerol (% w/v) | Glucose (% w/v) | Residuals | | |
|---|---|---|---|---|---|---|---|
| | | | | | Starch (% dw) | Protein (% dw) | Solids (% dw) |
| Corn flour (Regular) | 4266 | 14.11 | 0.84 | 0.02 | 16.56 | 24.59 | 11.29 |
| Corn flour (autoclaved) | 55 | 9.25 | 0.9 | 2.47 | 38.29 | 15.17 | 18.63 |

SYSTEMS AND METHODS FOR FEEDSTOCK QUALITY ASSESSMENT

CROSS-REFERENCE TO RELATED APPLICATIONS

This application is a U.S. national stage filing of Patent Cooperation Treaty (PCT) application serial number PCT/US11/63963 entitled "SYSTEMS AND METHODS FOR FEEDSTOCK QUALITY ASSESSMENT filed on Dec. 8, 2011, which claims the benefit of U.S. Provisional Application Ser. No. 61/421,454, filed Dec. 9, 2010, and entitled "SYSTEMS AND METHODS FOR FEEDSTOCK QUALITY ASSESSMENT. The entireties of the aforementioned applications are herein incorporated by reference.

FIELD

The subject disclosure relates to systems and methods for determining feedstock quality for use in ethanol production.

BACKGROUND

Ethanol may be produced from grain-based feedstocks (e.g., corn, sorghum/milo, barley, wheat, soybeans, etc.), from sugar (e.g., sugar cane, sugar beets, etc.), or from biomass (e.g., lignocellulosic feedstocks, such as switchgrass, corn cobs and stover, wood, or other plant material). The most common raw material for ethanol production, however, is the starch contained within corn.

In a conventional ethanol plant, corn kernels are cleaned and milled to prepare starch-containing material for processing. Corn kernels may also be fractionated to separate the starch-containing material (e.g., endosperm) from other matter (such as fiber and germ). The starch-containing material is slurried with water and liquefied to facilitate saccharification, where the starch is converted into sugar (e.g., glucose), and fermentation, where the sugar is converted by an ethanologen (e.g., yeast) into ethanol. The fermentation product is beer, which comprises a liquid component, including ethanol, water, and soluble components, and a solids component, including unfermented particulate matter (among other things). The fermentation product is sent to a distillation system where the fermentation product is distilled and dehydrated into ethanol. The residual matter (e.g., whole stillage) comprises water, soluble components, oil, and unfermented solids (e.g., the solids component of the beer with substantially all ethanol removed, which may be dried into dried distillers grains (DDG) and sold, for example, as an animal feed product). Other co-products (e.g., syrup and oil contained in the syrup), may also be recovered from the whole stillage. Water removed from the fermentation product in distillation may be treated for re-use at the plant.

Many traditional corn to ethanol production facilities employ high heat to cook (gelatinize) the starch-containing material to facilitate liquefaction prior to saccharification. One result from the cooking of the starch slurry is that endogenous enzymes, which are native to the corn, are rendered inoperative. Thus, in cooked systems, corn quality has traditionally been purely defined by the total fermentable starch content of the corn. However, as non-cooking processes (raw starch hydrolysis) become more prevalent, it has become clear that good quality corn is no longer merely synonymous with starch content. In these ethanol production plants, the slurry is subjected to simultaneous saccharification and fermentation. There is abundant evidence of presence of esterases in grains (Ward and Bamforth, 2002). The endogenous esterase activity in grains can serve as an indicator for the activities of specific enzymes present in the feedstock (such as amylases and endoproteases). (Jones, 2005). Since the activity of endogenous enzymes within feedstock grains has been linked to the temperature that the grains are subjected to, when non-cooked ethanol production is utilized, the endogenous enzyme activity may significantly impact saccharification efficiency. (Kumar et al., 2005). Thus, corn or other feedstock which retain high levels of endogenous enzymes are found to produce higher fermentation efficiencies. (Setiawan et al., 2010). Again, this is due in part to the fact that the naturally present enzymes are preserved and therefore aid in the saccharification process.

In addition to ethanol production, assessment of feedstock quality, as indicated by endogenous enzyme activity, may have a large impact upon other applications of the feedstock. Prominently, feedstock quality may be directly correlated to germination efficiency of seed quality feedstock. Further, for wet millers, it may be advantageous to have feedstock with higher endogenous enzyme activity, as more active feedstock may process better in a wet mill.

Currently there is no rapid and effective method available to determine quality of corn based on the levels of endogenous enzymes present. Instead, routine quality tests such as moisture content, presence of foreign material, broken grain, and test weight are performed on the incoming corn. (Evers et al., 2002). However, those tests do not indicate if the corn has more enzyme activity (such as amylases which convert starch into sugars), and thus have higher saccharification efficiency. (Ziegler, 1999). Recently, there has been renewed interest in developing Near Infrared Spectroscopy (NIR) methods for assessing the fermentable starch in superior corn hybrids by companies such as DuPont Pioneer; however, such systems are still under development, and show poor correlation between NIR readings and corn fermentation yields.

SUMMARY

In some embodiments, systems and methods for assessing quality of feedstock include providing a sample containing flour. The flour is ground feedstock and, in some embodiments, may include a grind that is greater than 90% fines. In some cases, the flour is diluted in water for the assessment. Additionally, in some embodiments, the flour is buffered with a phosphate buffered saline solution.

In some embodiments, the buffered flour solution is brought into contact with a molecule, or fluorescent dye, that is altered by enzymatic activity in a detectable fashion. The enzymatic activity detected is an esterase activity, which indicates the general viability of endogenous enzymes in the feedstock sample, in some embodiments. The molecule may include at least one of fluorescein diacetate and/or difluorofluorescein. After esterase activity on these molecules, fluorescein is generated. Fluorescein is fluorescent, and may be measured using a fluorometer. Enzyme activity may be facilitated using an incubator. The use of fluorescein diacetate for the purposes of quantifying microbial vitality, by way of enzyme activity measurement, is known. However, fluorescein diacetate has never been previously utilized to determine enzyme levels in feedstock materials.

In some embodiments, it may be beneficial to perform two incubations and fluorescence measurements. By subtracting the difference between the measured fluorescence, a fluorescence index may be found, which correlates well with the endogenous enzyme activity in the feedstock sample.

Endogenous enzyme activity relates to ethanol yields from the raw starch hydrolysis of the feedstock, and may thus be used to define quality of the feedstock.

Note that the various features of the disclosed aspects described herein may be practiced alone or in combination. These and other features of the one or more aspects will be described in more detail below in the following detailed description and in conjunction with the following figures.

DESCRIPTION OF THE DRAWINGS

In order that the disclosed aspects may be more clearly ascertained, some embodiments will now be described, by way of example, with reference to the accompanying drawings, in which.

DESCRIPTION OF THE EMBODIMENTS

The various aspects will now be described in detail with reference to several embodiments thereof as illustrated in the accompanying drawings. In the following description, numerous specific details are set forth in order to provide a thorough understanding of the various embodiments. It will be apparent, however, to one skilled in the art, that embodiments may be practiced without some or all of these specific details. In other instances, well known process steps and/or structures have not been described in detail in order to not unnecessarily obscure the various embodiments. The features and advantages of embodiments may be better understood with reference to the drawings and discussions that follow.

The one or more aspects relate to systems and methods for assessing the quality of feedstock starch materials. An urgent need exists for a system and method for determining feedstock quality for ethanol production based upon endogenous enzyme levels. Such a system would provide a fast and efficient quantitative assessment of corn quality relating to ethanol yields. Such a system may be relied upon for purchase contracts and to determine quality of corn prior to fermentation.

The quantitative assessment of feedstock may be based upon endogenous enzymes present in the feedstock starch materials or grain material. Much of the disclosure will center on the use of feedstock in use as a raw material for ethanol production. Note, however, that any downstream application where it is desirable to determine the endogenous enzyme levels in feedstock falls within the scope of this application. For example, when feedstock is utilized as a nutritional supplement it may be advantageous to know the endogenous enzyme quality of the feedstock. Likewise, knowledge of feedstock quality may be beneficial when dealing with seed quality material, in wet mills, and in other manufacturing applications.

In a similar vein, much of the feedstock discussed in this application includes corn kernels. While corn is of particular interest in use for some applications of ethanol production, the subject disclosure is intended to be equally applicable to all sources of feedstock, including, for example, sorghum/milo, barley, wheat, soybeans, and the like. The discussions of feedstock including corn are thus entirely for clarification and exemplary purposes.

Figure 1:
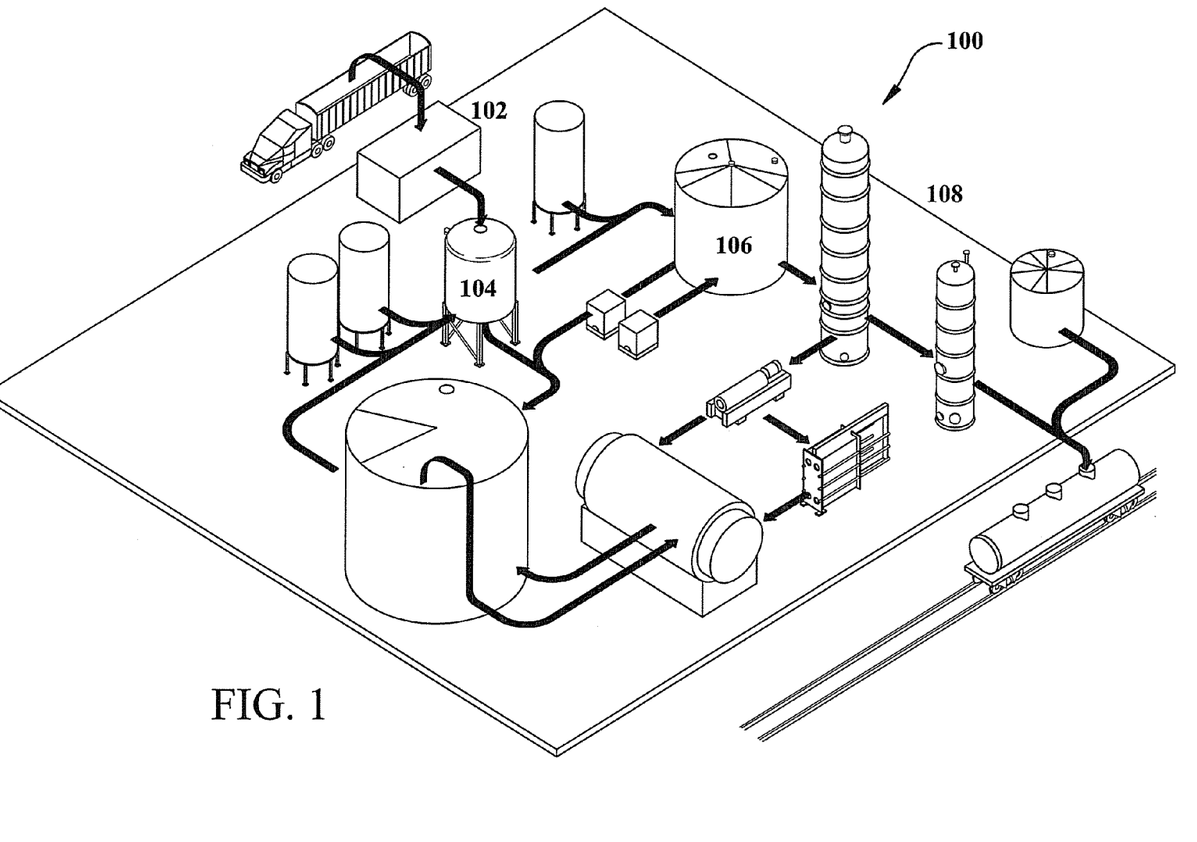
FIG. 1 is a perspective view of a biorefinery comprising an ethanol production facility in accordance with some embodiment.

To facilitate discussion, FIG. 1 illustrates an example biorefinery 100 comprising an ethanol production facility configured to produce ethanol from corn. The example biorefinery 100 comprises an area 102 where corn (or other suitable material including, but not limited to, biomass, sugars, and other starch products) is delivered and prepared to be supplied to the ethanol production facility. The ethanol production facility comprises apparatus 104 for preparation and treatment (e.g., milling) of the corn into corn flour suitable for fermentation into fermentation product in a fermentation system 106. The ethanol production facility comprises a distillation system 108 in which the fermentation product is distilled and dehydrated into ethanol. The biorefinery may also comprise, in some embodiments, a by-product treatment system (shown as comprising a centrifuge, a dryer, and an evaporator).

In some embodiments, the system for assessing the quality of feedstock may be present at the biorefinery for use on raw incoming corn (or other feedstock). The outcome of the quality assay may be useful in predicting the ethanol yield from a given batch of corn product. In some embodiments, very poor quality corn may be separated; therefore enabling only higher quality corn to be processed. Low quality corn may then be added in small dosages to batches of higher quality corn to generate more consistent, and generally higher, ethanol yields. Low quality corn may alternatively be resold or diverted to some other downstream purpose, in some embodiments. Likewise, the feedstock quality assessment system may be useful at market, in the field, or at a transportation stop in order to assess corn quality before being sent to an ethanol production facility.

Figure 2A:
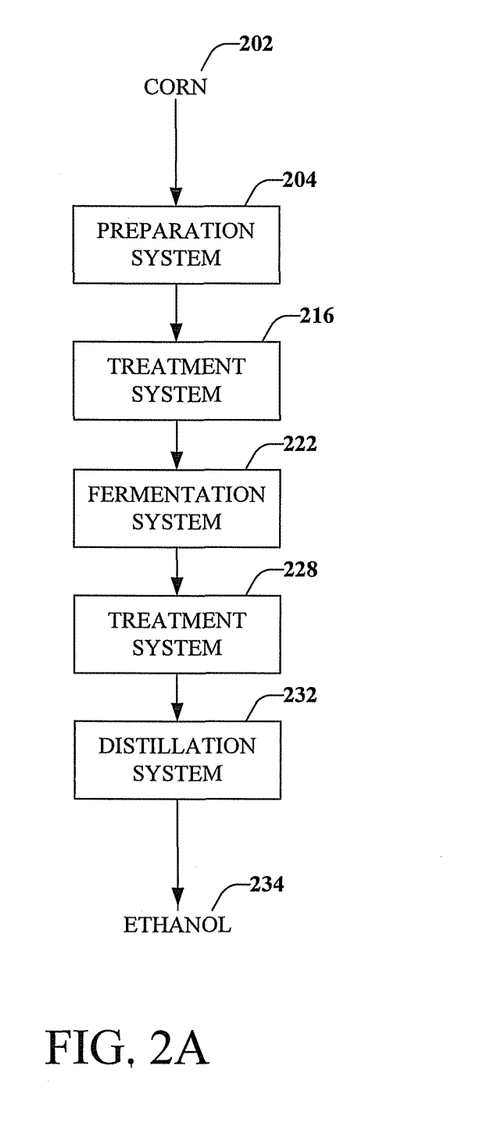
FIGS. 2A-2B are schematic block diagrams of ethanol production processes, in accordance with some embodiments.
Figure 2B:
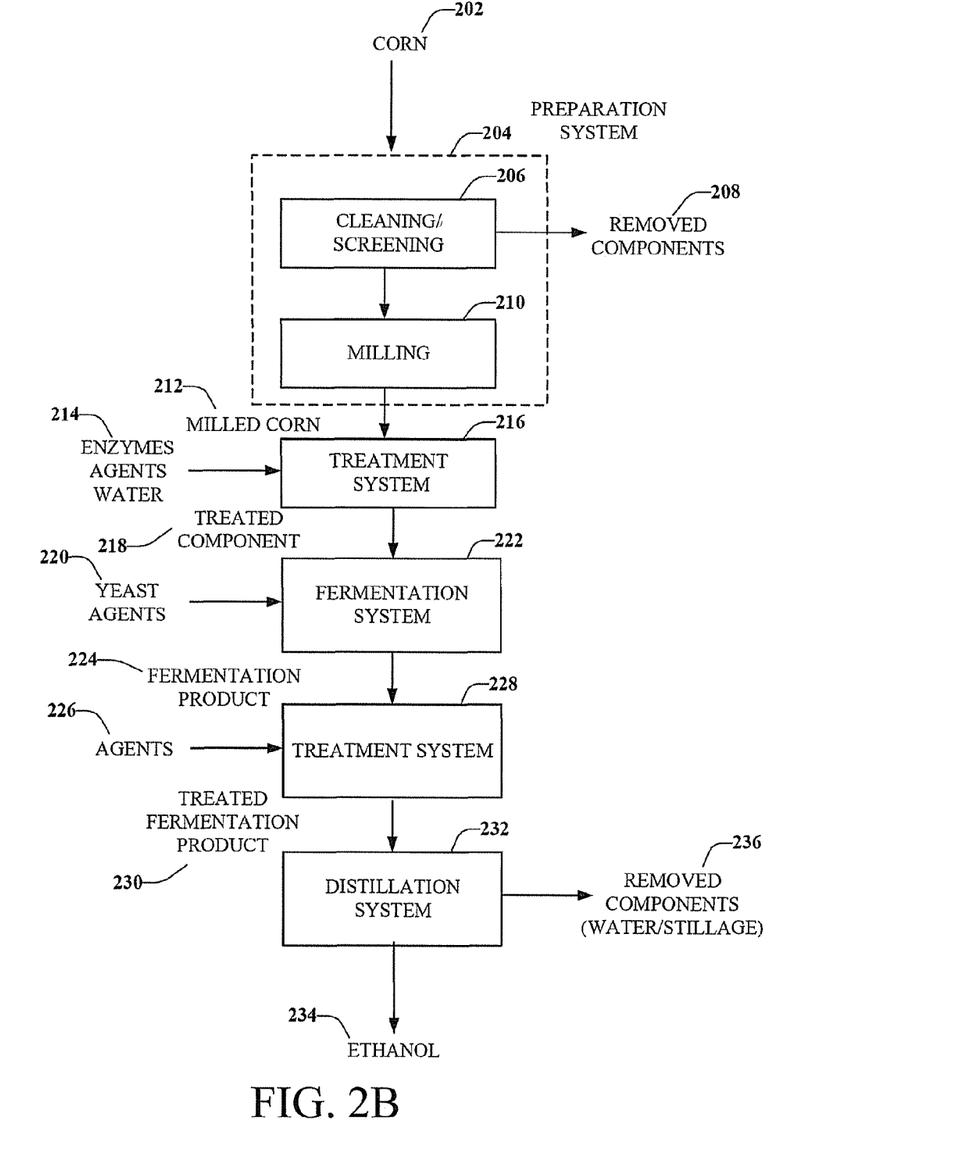

Referring to FIGS. 2A-2B, in an ethanol production process, corn 202 (or other suitable feed material) may be prepared for further treatment in a preparation system 204. As seen in FIG. 2B, the preparation system 204 may comprise cleaning or screening 206 to remove foreign material, such as rocks, dirt, sand, pieces of corn cobs and stalk, and other unfermentable material (e.g., removed components 208). After cleaning or screening 206, the particle size of corn may be reduced by milling 210 to facilitate further processing. The corn kernels may also be fractionated into starch-containing endosperm, fiber, and germ, in accordance with some embodiments. The milled corn 212 or endosperm is slurried with water, enzymes and agents 214 to facilitate the conversion of starch into sugar (e.g. glucose), such as in a first treatment system 216. The sugar (e.g., treated component 218) is converted into ethanol by an ethanologen (e.g. yeast or other agents 220) in a fermentation system 222. The product of fermentation (fermentation product 224) is beer, which comprises a liquid component, including ethanol and water and soluble components, and a solids component, including unfermented particulate matter (among other things). The fermentation product 224 may be treated with agents 226 in a second treatment system 228. The treated fermentation product 230 is sent to a distillation system 232. In the distillation system 232, the (treated) fermentation product 230 is distilled and dehydrated into ethanol 234. In some embodiments, the removed components 236 (e.g., whole stillage), which comprise water, soluble components, oil and unfermented solids (e.g., the solids component of the beer with substantially all ethanol removed), may be dried into dried distillers grains (DDG) in a third treatment system (where the removed components may be treated with agents) and sold as an animal feed product. Other co-products, for example, syrup (and oil contained in the syrup), may also be recovered from the stillage. Water removed from the fermentation product in distillation may be treated for re-use at the plant.

Figure 3:
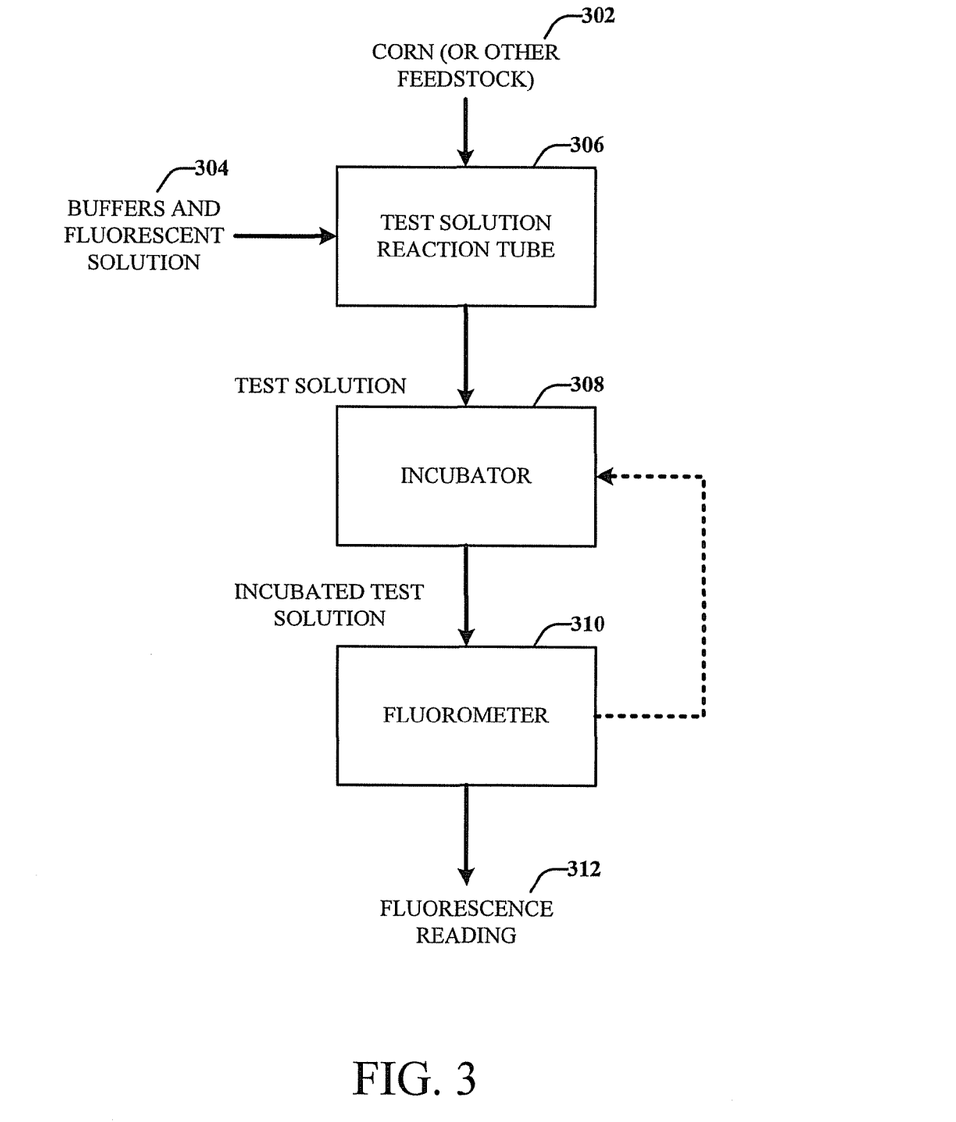
FIG. 3 is an example schematic block diagram of a system for assessing the quality of feedstock, in accordance with some embodiments.

Referring now to FIG. 3, an example schematic block diagram of a system for assessing the quality of feedstock is shown. The entire assessment procedure is intended to be completed rapidly, often in five minutes or less per sample. In this example system, corn 302 or other feedstock may be combined with buffers and a fluorescent solution 304 in a reaction vessel 306. The test solution may then be incubated in an incubator 308. The incubated solution may fluoresce in response to endogenous enzyme activity in the feedstock.

A fluorometer 310 may then be utilized in order to measure fluorescence levels 312. An initial fluorometer reading may equate to endogenous enzyme activity, as well as functioning as a baseline measurement for fluorescence. In some embodiments, it may be advantageous to return the samples for further incubation after baseline fluorometer reading (as shown by the dotted feedback loop). The sample may then be measured again after the second incubation. The baseline measurement may be subtracted from the second measurement to determine a change in fluorescence. This change in fluorescence may, in some embodiments, relate directly to the activity of endogenous enzymes within the test solution. These raw fluorescence numbers may then be compared against cutoffs, or calibrated, in order to provide a quantitative measurement of feedstock quality.

Figure 4:
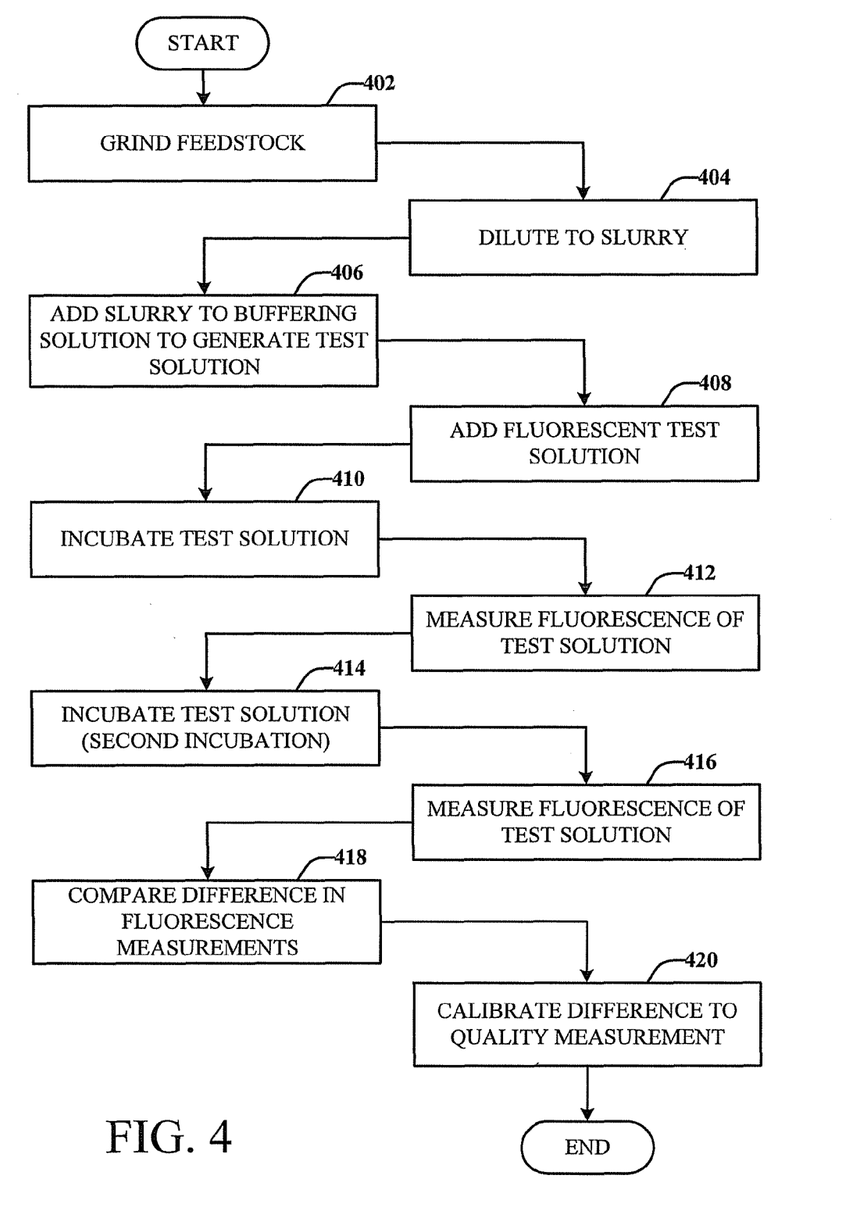
FIG. 4 is an example flowchart for a method of assessing a quality of feedstock, in accordance with some embodiments.

FIG. 4 provides a more detailed example flowchart for the process of assessing the quality of feedstock, in accordance with some embodiments. In this exemplary process, the feedstock matter (e.g. corn, wheat, or other starch material) may be ground (at 402) to a sufficiently fine particle size to facilitate the assay. In some embodiments, the level of grinding may be similar to the grinding being performed on the feedstock for ethanol production. In these embodiments, it may be advantageous to randomly sample the grind being prepared for ethanol production in order to generate feedstock quality data. In some embodiments, the grind is greater than 90% fines. From the grind, a known quantity of the ground flour may be taken and diluted (at 404) in water, or other buffering solution. In some embodiments, 0.5 grams of flour may be diluted in 10 milliliters of water, or other buffer, to generate the diluted flour slurry.

Some of the diluted slurry may then be utilized as the sample for the assay. In some embodiments, some portion of the diluted sample slurry is added to a buffering solution (at 406). In some embodiments, 0.5 milliliter of buffer may be combined with 50 μL of the diluted sample slurry. In some embodiments, the buffer may include a phosphate buffered saline. In some particular embodiment, the buffer may be generated from a 10× stock solution comprising (per liter) roughly:

80 grams NaCl
2 gram KCl
14.4 grams $Na_2HPO_4$
2.4 grams $KH_2PO_4$

In these embodiments, the stock buffer solution pH may be adjusted to roughly 7.4 using NaOH. Note that other deviations or formulations of the buffering solution are considered within the scope of some embodiments.

In addition to the buffering solution and diluted sample slurry, a fluorescent test solution may be combined in the reaction vessel (at 408). In some embodiments, the fluorescent test solution includes Fluorescein diacetate, difluorofluorescein, or some equivalent. In some particular embodiments, the fluorescent test solution includes 30 mg of Fluorescein diacetate in 10 mL of Acetone. In some embodiments, roughly 50 μL of the fluorescent test solution may be added per 0.5 milliliter of the buffer solution indicated above. Fluorescein diacetate is not fluorescent, but when it comes in contact with esterases these enzymes cleave the compound to yield fluorescein, which is fluorescent. The intensity of fluorescence is directly proportional to the esterase activity in the grain cleaving the Fluorescein diacetate.

The solution of sample slurry, buffer and fluorescein diacetate is mixed, and then incubated (at 410). Incubation, in some embodiments, may be for roughly one minute. In some embodiments, incubation may also be at or about 30 degrees Celsius. Other temperatures may be utilized; however, it is beneficial to have a sufficiently high temperature to facilitate enzymatic activity, and lower than the temperature which renders the enzymes inoperable.

After incubation, the sample is again mixed via agitation or inversion. A first baseline measurement of fluorescence may be taken (at 412). The measurement of fluorescence may be made using any fluorometer (spectrofluorometer) that is enabled to measure fluorescence at specific wavelengths for detection of the dyes employed in the system. In some embodiments, the spectrofuorometer may be enabled to operate with an excitation wavelength of about 494 nm and detect an emission wavelength of about 521 nm. For example the hand held fluorometer "Picofluor" manufactured by Turner Designs of Sunnyvale, Calif., may suited for use in some embodiments.

After baseline fluorescence is measured, the sample may be incubated a second time (at 414). In some embodiments, the second incubation may be for a two minute duration. In some alternate embodiments, other incubation times are considered. Likewise, the temperature of the incubation may be 30 degrees Celsius, or some other acceptable temperature, as noted above. It is important to note that length/temperature of incubation, as well as endogenous enzyme content of the sample, determines how much of the Fluorescein diacetate is cleaved into fluorescein. Thus, activity quantifications (quality analysis) may be calibrated according to amount of sample processed and incubation time and temperature.

Figure 13:
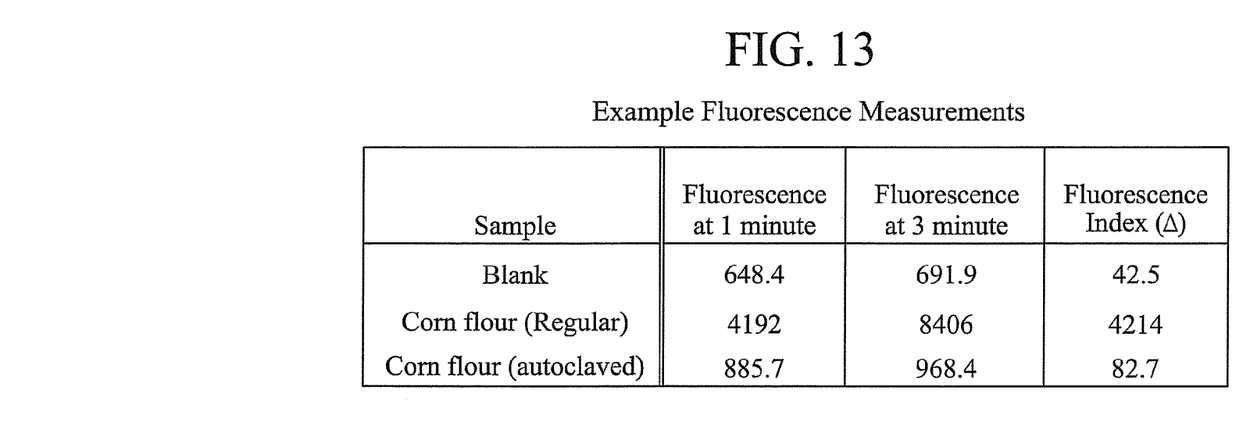
FIG. 13 is an example table illustrating fluorescence measurements over time, in accordance with some embodiments.

After the second incubation, the samples may again be mixed and the fluorescence measured (at 416). The second fluorescence measurement is typically higher as a function of enzyme activity. Thus, the difference between the baseline fluorescence measurement and the second measurement may be calculated, thereby reflecting endogenous enzyme activity (at 418). An example of the fluorescence measurements taken after the initial incubation and second incubation are illustrated in FIG. 13 where three example samples are shown measured, including a blank sample, a corn sample, and an autoclaved corn sample. The blank sample is a control sample. The autoclaved corn sample mimics corn that undergoes cooking during liquefaction. The regular corn flour is what is present in a non-cooked (raw starch hydrolysis) plant. Of note is that the blank and autoclaved corn had much lower fluorescence measurements than the non-cooked corn sample. Further, the difference between the baseline fluorescence measurement and the second fluorescence measurement (fluorescence index) is also much higher for the regular corn in this example.

Figure 14:
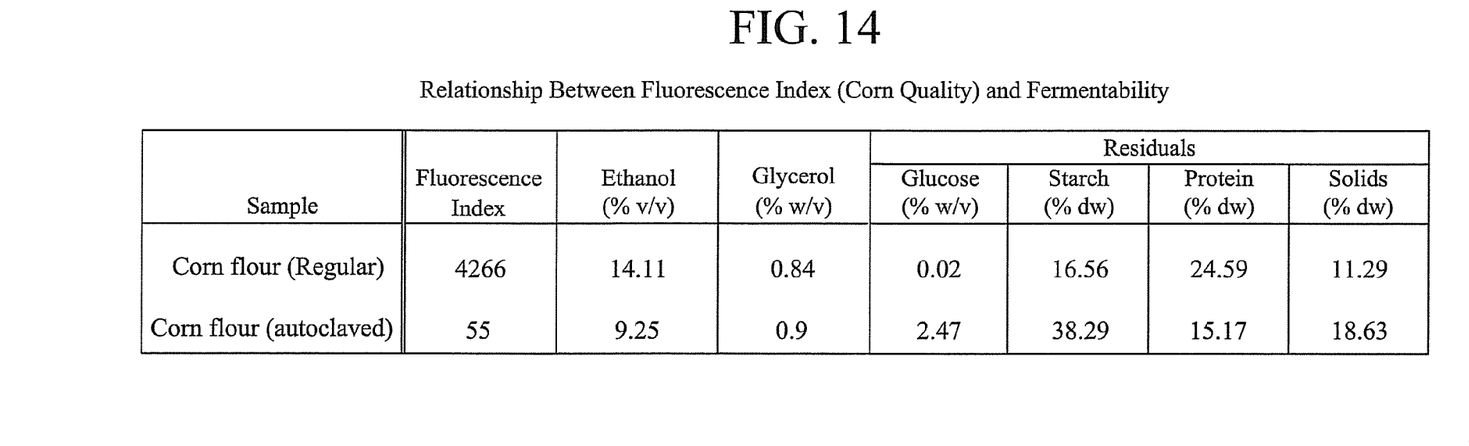
FIG. 14 is an example table illustrating a relationship between fluorescence and fermentability in corn, in accordance with some embodiments.

Returning to FIG. 4, the fluorescence index (which relates to enzyme activity) may then be correlated to fermentation yields using calibration curves (at 420). Additionally, other factors such as fluorescence bleaching, and the like, may be calibrated for in this final step. In such a manner, the quality of feedstock may be readily determined in a rapid and efficient manner. FIG. 14 provides an example of the relationship between the fluorescence index and fermentability. In FIG. 14, the fermentation results of two samples are provided, along with the fluorescence index of the samples prior to fermentation. The non-cooked corn has a much higher fluorescence index in this example, equating to higher endogenous enzyme activity. The fluorescence index of the autoclaved corn is much lower since the cooking destroys the activity of endogenous enzymes. The ethanol content of the fermentation (fermentation yields) correlate to the endogenous enzyme activity; with the regular corn yielding significantly more ethanol than the autoclaved corn. This more complete fermentation by regular corn is reflected in the residuals: starch and glucose in the regular corn are much lower after fermentation as compared to the autoclaved corn.

As previously noted, knowledge of feedstock quality may be of benefit when pricing and purchasing materials for a wide range of downstream applications. As it relates to the ethanol industry, only higher quality corn may be purchased (or demand a premium at purchase). Lower quality corn may be segregated and added in slowly to batches of higher quality corn in order to increase overall ethanol yields. In the farming industry, only higher quality seeds may be utilized for crop planting. From the growers' perspective, a quality analysis may be utilized to generate higher quality corn through plant selection and post harvest conditions. For example, it has been shown that drying corn at high temperatures for prolonged time may reduce corn quality. (Setiawan et al., 2010). The same is likely true for other feedstock. (Kumar et al., 2005). The drying temperatures which reduce feedstock quality may vary, however, dependent upon crop species and strain. A grower may utilize rapid feedback of feedstock quality to implement procedures and crop selection in order to increase quality in future harvests.

Further, by readily quantifying the quality of feedstock, it may be possible to alter the feedstock to be of higher quality. For example, brewers have learned to take advantage of the natural endogenous enzyme activity of germinated barley. This is accomplished using malted barley prepared from the malting process. The process begins by steeping barley under controlled conditions to increase the moisture content and oxygenating to stimulate the dormant kernels natural metabolic processes, which function to increase enzyme activity in the aleurone layer. The barley is then allowed to germinate. Enzymes such as β-amylase, protease (exo-peptidase, carboxy-peptidase, endo-proteases), β-glucanase, α-amylase, and pentosanase are formed in the aleurone layer of the barley during malting. Formation and induction (activation) of these enzymes is promoted by the moisture and oxygen present in the steep tanks. Endogenous enzyme activity increases considerably (perhaps 5× to 15×) during the germination process. In some cases, the received feedstock may be subjected to similar conditions to aid in the production of endogenous enzymes, thereby increasing the quality assessment. This may be particularly helpful when an ethanol producer, for example, received low quality feedstock and wishes to increase ethanol production yields.

A series of limited examples were conducted according to an exemplary embodiment of the system (as shown in FIG. 3) in an effort to determine suitable apparatus and operating conditions for the assessment of corn quality. The following examples are intended to provide clarity to some embodiments of systems and means of operation; given the limited nature of these examples, they do not limit the scope of the various aspects.

EXAMPLE 1

The feedstock assessment system (as shown in FIG. 3) may be used to assess the quality of corn for use as a material for fermentation to yield ethanol. In this example, 70 corn samples were tested for quality using the disclosed methods. The corn samples were dried at varying temperatures to determine effects on corn quality. For each drying temperature, 14 replicate samples were performed. Drying temperatures were at 120°, 140°, 160°, 180°, and 200° Fahrenheit. After assessment for corn quality, the samples were fermented in order to illustrate the correlation between the corn quality assessment and the fermentation yields.

For the feedstock quality assessment, the corn flour is ground fine (>90% fines) as it would be used in a raw starch simultaneous saccharification and fermentation. A known quantity of this flour (0.5 g) is placed in a 15 mL centrifuge tube and diluted to the 10 mL mark with de-ionized water. This diluted slurry is used as the sample. Next, 500 μL of a phosphate buffered saline is added into a glass sample vial. To this, 50 μL of 30 mg of Fluorescein diacetate in 10 mL of Acetone solution is added. To this mixture, 50 μL of the corn slurry sample to be analyzed is added. Then the sample vial is capped, inverted three times, and placed immediately in the incubator (at 30 degrees Celsius) for 1 minute. After this first incubation, the sample is removed from the incubator, inverted three times, and placed in a fluorometer to measure fluorescence. The vial is immediately placed back into the incubator for an additional 2 minutes. After the second incubation, the vial is removed, inverted three times, and placed in a fluorometer to measure fluorescence.

Figure 5:
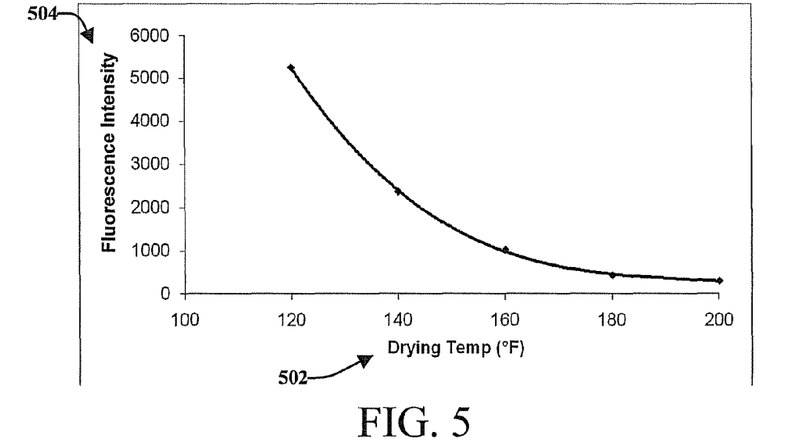
FIG. 5 is an example plot diagram comparing drying temperature of corn samples to a measured fluorescence intensity, in accordance with some embodiments.

Then, the Δ fluorescence (referred to as fluorescence index) is calculated and recorded for the sample. FIG. 5 is an example plot diagram 500 comparing drying temperature 502 of corn samples (represented along the horizontal axis) to the measured fluorescence intensity 504 (represented along the vertical axis) for the 70 samples. Here each data point is the averages for the 14 samples dried at the given temperature. The higher the difference in fluorescence, the more the esterase activity within the sample. Esterase activity is an indication of higher endogenous enzyme activity in the grain. Higher endogenous enzyme activity in the grain correlates to better fermentability/ethanol production in a raw starch process. As shown, there is a marked decrease in corn quality (as measured by the fluorescence index) as the temperature of drying increases. This is due to damage to the endogenous enzymes as temperatures are increased.

After the feedstock quality assessment was completed, the samples were fermented in order to illustrate the correlation between the fluorescence index (quality assessment or quality designation) and actual ethanol yields. Fermentation included adding deionized water to the corn flour to generate a slurry, adjusting pH, and adding enzymes for saccharification. Fali yeast in the active dry form was added. A typical temperature staging protocol was practiced during the fermentation. Samples were withdrawn periodically at 24 and 71 hours. These samples were then analyzed for sugars, organic acids and ethanol using the High Performance Liquid Chromatography (HPLC).

Figure 6A:
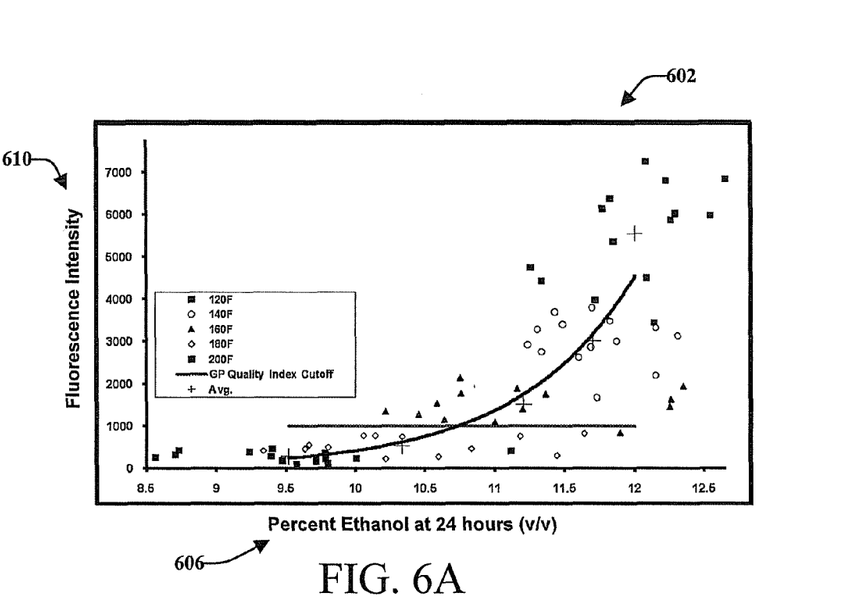
FIGS. 6A-6B are example plot diagrams comparing percent ethanol yields after fermentation of corn samples to the measured fluorescence intensity at 24 hours and 71 hours of fermentation, respectively, in accordance with some embodiments.
Figure 6B:
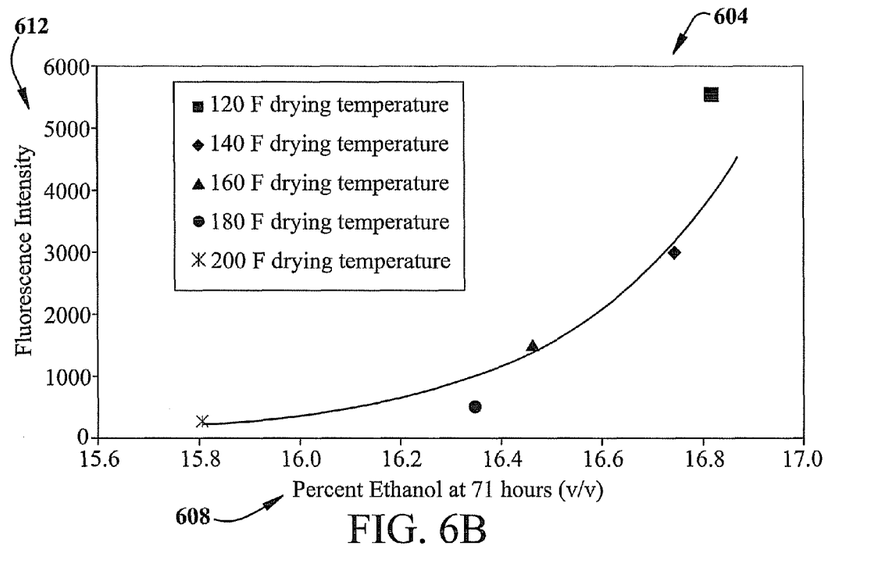

FIGS. 6A-6B are example plot diagrams 602 and 604 comparing percent ethanol yields 606 and 608 (represented along the horizontal axes) after fermentation of corn samples to the measured fluorescence intensity 610 and 612 (represented along the vertical axes) at 24 hours and 71 hours of fermentation, respectively. FIG. 6A illustrates the data points for all 70 samples after 24 hours of fermentation; included in the plot is a line indicating "quality index cutoff" under which samples are considered to be of "bad" quality (i.e. a fluorescence index of less than 1000). It is clear that higher fluorescence index values strongly correlate to higher ethanol fermentations. This trend continues after 71 hours of fermentation, as indicated at the plot of FIG. 6B. The data points on the 71-hour fermentation plot are averages of 14 samples relating to each drying temperature.

Figure 7:
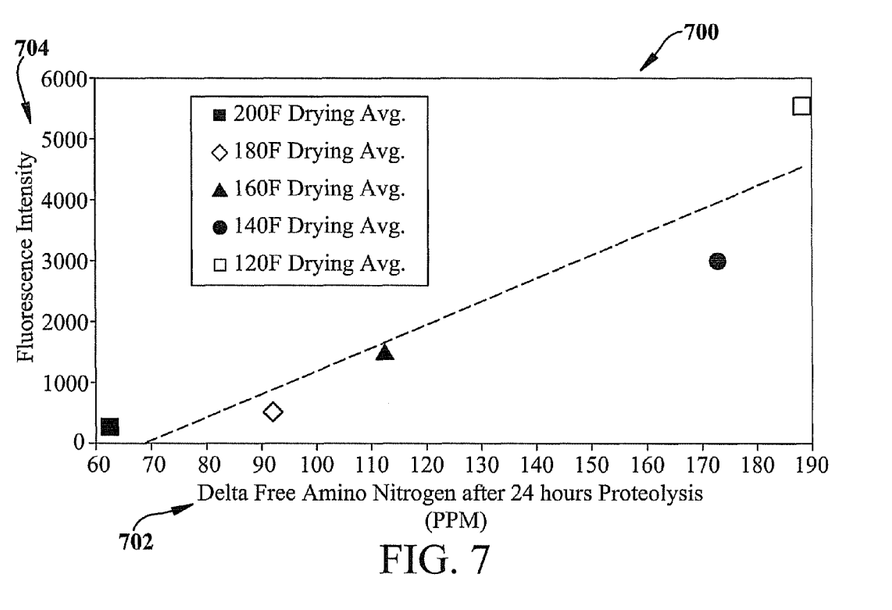
FIG. 7 is an example plot diagram comparing delta free amino nitrogen after proteolysis to a measured fluorescence intensity, in accordance with some embodiments.

Additionally, samples were slurried and incubated without yeast to measure glucose production. Samples were withdrawn at 0 h and 24 h and analyzed for free amino nitrogen production by the Ninhydrin method (American Society for Brewing Chemists Methods of Analysis, 8$^{th}$ edition, 1992). The difference (Δ) between the 24 h and 0 h data is a good indication for changes in the free amino nitrogen in the samples. It is known that exogenous proteases increase free amino nitrogen. (Taylor et al., 1986). Similarly, the endogenous enzyme (endoproteases in particular) activities in the samples result in increases in free amino nitrogen. FIG. 7 is an example plot diagram 700 comparing delta free amino nitrogen (FAN) after proteolysis to the measured fluorescence intensity. A linear relationship is evident between the endogenous protease activity 702 (Δ Free amino nitrogen), represented on the horizontal axis and the fluorescent index 704, represented on the vertical axis, for each sample.

This generation of free amino nitrogen in the raw starch (non-cooked) process helps with providing the nitrogen requirement for the fermenting organism (yeast). Due to the provision of nitrogen in the form of amino acids, a reduction in glycerol formation by the yeast is observed in the raw starch process. Therefore, while processing better quality grain with higher endogenous protease activity (which can be related to the esterase levels as a fluorescence index), no additional nitrogen supplementation in the form of ammonia or urea should be required in these embodiments.

Figure 8:
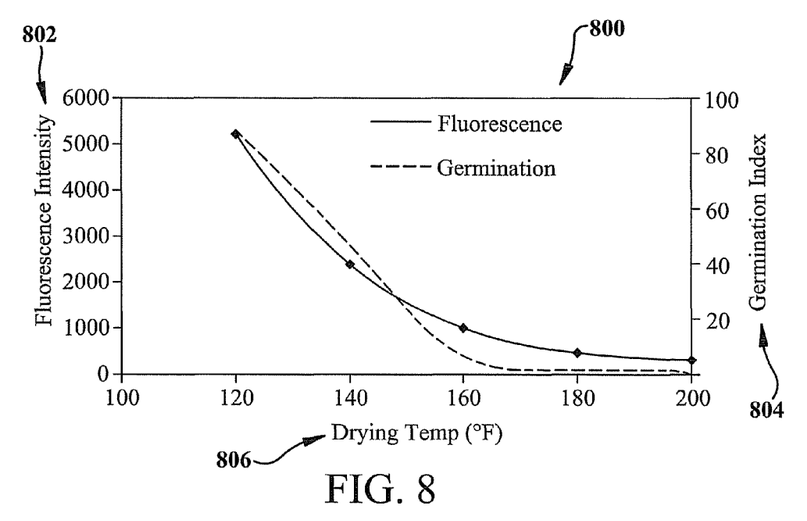
FIG. 8 is an example plot diagram comparing measured fluorescence intensity and germination index by drying temperatures for corn samples, in accordance with some embodiments.

In addition, the viability of corn samples, as indicated by germination rates, were measured for the corn samples dried at various temperatures. The germination rates where then compared against the fluorescence index for the same samples in order to correlate the quality assessment to corn viability. Germinations were performed by placing whole corn kernels in a moist wrapping for a known period of time and temperature. One hundred corn kernels were germinated in this fashion per sample in order to generate a germination index (i.e., percentage of kernels which germinate). FIG. 8 is an example composite plot diagram 800 comparing measured fluorescence intensity 802 and germination index 804, each represented on the vertical axis, by drying temperatures 806, represented on the horizontal axis, for corn samples. The solid line represents the average fluorescence index for all samples by drying temperature. The dashed line indicates the germination index average for all samples at the given drying temperature. It is clear that as drying temperature increases the quality decreases, as measured by the fluorescence index. Similarly, with increase in drying temperature there is a marked decrease in germination of the samples. Thus, fluorescence index and germination may be correlated to one another.

Figure 9:
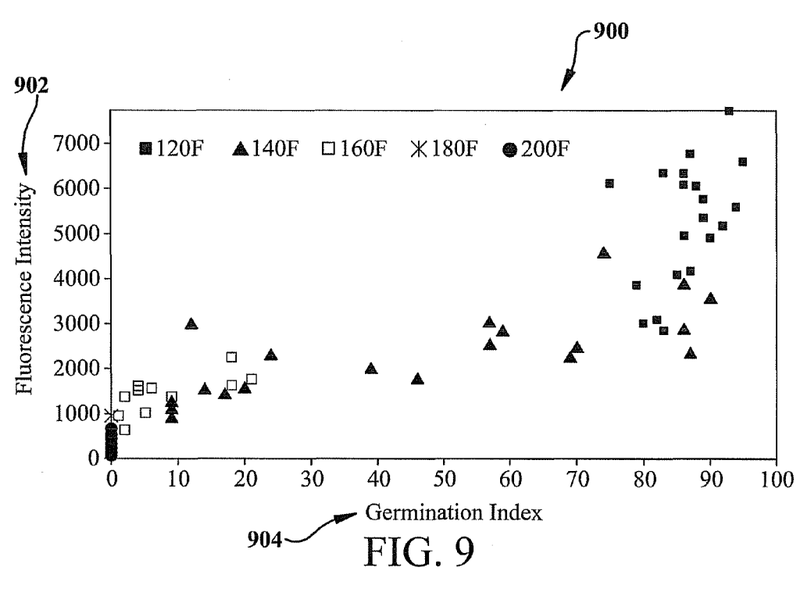
FIG. 9 is an example plot diagram comparing measured fluorescence intensity by germination index for corn samples at differing drying temperatures, in accordance with some embodiments.

This correlation may be seen in FIG. 9 as well, where an example plot diagram 900 comparing measured fluorescence intensity 902, represented on the vertical axis, with germination index 904, represented on the horizontal axis, for corn samples at differing drying temperatures. The samples at each drying temperature are indicated with differing plot designations. In this example graph, substantially only samples with a fluorescence index of greater than 3000 have a germination rate of 80% or higher. Again, it is clear that these samples are all dried at lower temperatures. For a seed buyer, or producer, the ability to rapidly correlate feedstock quality through the disclosed systems and methods to rate of germination could be highly valuable.

EXAMPLE 2

Additionally, a series of experiments were performed in order to exemplify that the current feedstock quality assessment system is measuring esterase activity. In the second example experiment for illustrating that esterase is in fact being measured by the quality assessment system, an inhibitor for esterase, phenyl carbamate, was identified. Phenyl carbamate is well known as an esterase inhibitor, and was added to samples of good quality corn samples in varying concentrations in order to illustrate that esterase activity is causally related to fluorescence when using the above mentioned feedstock quality assessment system.

In this example, water was used as the solvent for phenyl carbamate. Three different solutions of phenyl carbamate in water were prepared at 0.025, 0.05, and 0.1% w/v respectively. These solutions were used in the samples to study the inhibition of esterase activity. The samples for the assay then included: (i) 0.25 g corn in 10 mL deionized water, (ii) 0.25 g corn in 10 mL of 0.025% phenyl carbamate, (iii) 0.25 g corn in 10 mL of 0.05% phenyl carbamate, and (iv) 0.25 g corn in 10 mL of 0.1% phenyl carbamate.

Figure 10:
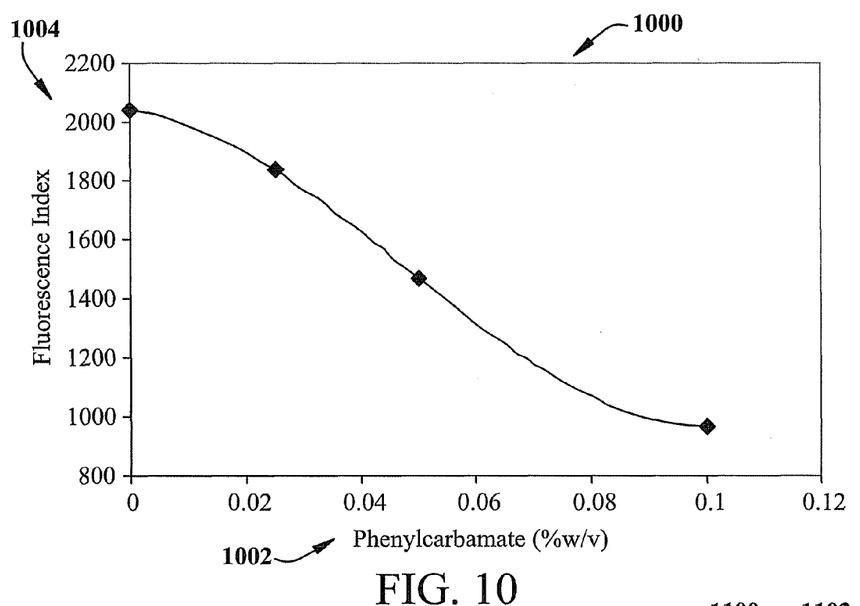
FIG. 10 is an example plot diagram comparing measured fluorescence intensity for corn samples subjected to treatment by esterase inhibitor at various levels, in accordance with some embodiments.

Each of the four samples and a reagent blank were assayed in triplicate. The results confirm the inhibition of esterase activity by phenyl carbamate is directly related to lower fluorescence activity by the feedstock assessment system. FIG. 10 provides a plot diagram 1000 for the results of this example experiment. As can be seen, with increased loading of the phenyl carbamate 1002 (represented along the horizontal axis) the fluorescence 1004 (represented along the vertical axis) decreases due to the reduction in esterase activity via inhibition.

EXAMPLE 3

Figure 11:
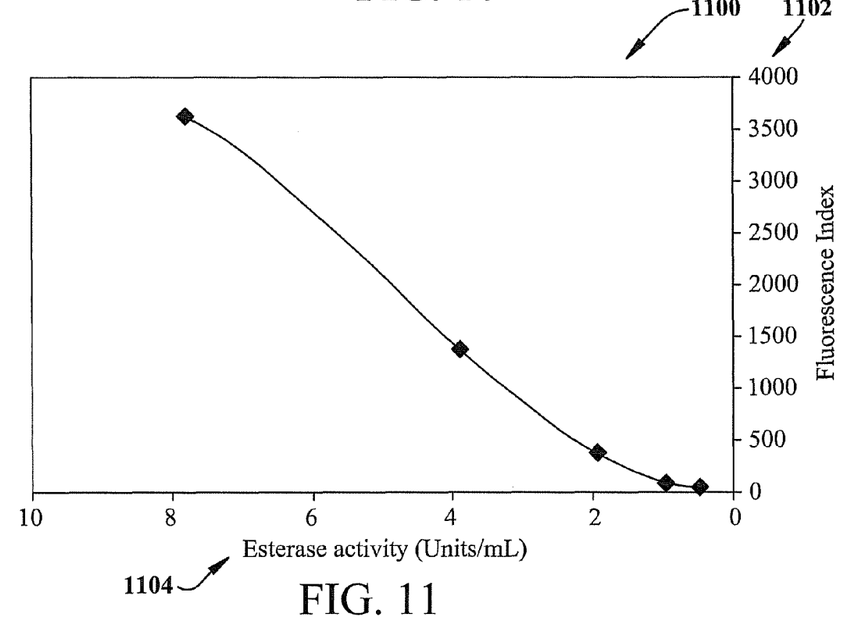
FIG. 11 is an example plot diagram comparing measured fluorescence intensity for differing concentrations of esterase solutions, in accordance with some embodiments.

A further example experiment was performed to exemplify that the current feedstock quality assessment system is measuring esterase activity. The third example experiment was designed such that isolated esterase is loaded in solution for analysis by the feedstock assessment system. Since purified corn esterase was not available, rabbit liver esterase (Sigma cat. no. E 0887) was obtained and used in this study. It is well known that this assay measures esterase activity in various microorganisms including yeast (Saccharomyces cerevisiae). The rabbit liver esterase is available at a concentration of 80 Units/mg. Therefore, a series of dilutions were prepared using the esterase in 10×PBS (phosphate buffered saline) to be able to obtain fluorescence intensity measurements within the limits of the measuring instrument. The results indicate that this assay does measure the esterase activity. FIG. 11 is an example plot diagram 1100 comparing measured fluorescence intensity 1002 (represented along the vertical axis) for differing concentrations of esterase solutions, in accordance with some embodiments. As can be seen, the fluorescence index 1002 to esterase activity 1004 (represented along the horizontal axis) followed a typical $3^{rd}$ order polynomial relationship.

EXAMPLE 4

Figure 12:
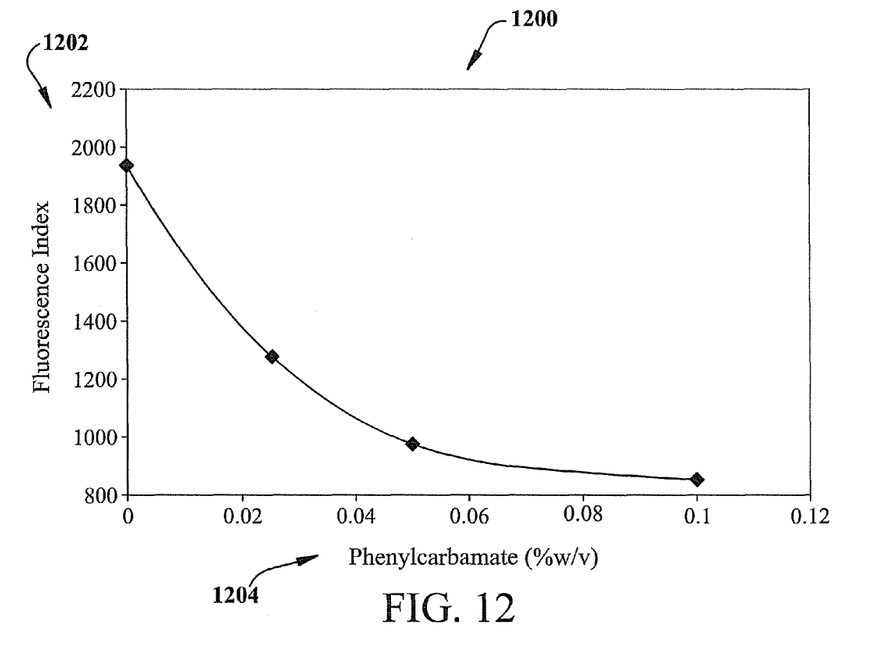
FIG. 12 is an example plot diagram comparing measured fluorescence intensity for esterase solutions subjected to treatment by esterase inhibitor, in accordance with some embodiments.

Lastly, a further example experiment was performed to study the inhibition of rabbit liver esterase using phenyl carbamate. For this example, a stock solution of the esterase was prepared in 10×PBS. A stock solution that had 50 units of esterase/mL was used to prepare the samples. The samples for the assay included: (i) 0.104 mL of esterase stock solution with 0.896 mL of 10×PBS (Control), (ii) 0.104 mL of esterase stock solution with 0.896 mL of 0.025% phenyl carbamate, (iii) 0.104 mL of esterase stock solution with 0.896 mL of 0.05% phenyl carbamate, (iv) 0.104 mL of esterase stock solution with 0.896 mL of 0.1% phenyl carbamate. Each of these four samples and a reagent blank were assayed in triplicate. FIG. 12 is a plot diagram 1200 showing the results of this example experiment. The fluorescence intensity 1202 is represented on the vertical axis and Phenyl carbamate 1202 is represented on the horizontal axis. The results showed inhibition of the esterase. A typical $3^{rd}$ order polynomial response was observed.

The results from these studies provide confirmation that the developed feedstock quality assay measures the esterase activity in the feedstock.

The embodiments as disclosed and described in the subject disclosure (including the FIGURES and Examples) are intended to be illustrative and explanatory of the disclosed aspects. Modifications and variations of the disclosed embodiments, for example, of the apparatus and processes employed (or to be employed) as well as of the compositions and treatments used (or to be used), are possible; all such modifications and variations are intended to be within the scope of the disclosed aspects.

The word "exemplary" is used to mean serving as an example, instance, or illustration. Any embodiment or design described as "exemplary" is not necessarily to be construed as preferred or advantageous over other embodiments or designs, nor is it meant to preclude equivalent exemplary structures and techniques known to those of ordinary skill in the art. Rather, use of the word exemplary is intended to present concepts in a concrete fashion, and the disclosed subject matter is not limited by such examples.

The term "or" is intended to mean an inclusive "or" rather than an exclusive "or." To the extent that the terms "comprises," "has," "contains," and other similar words are used in either the detailed description or the claims, for the avoidance of doubt, such terms are intended to be inclusive in a manner similar to the term "comprising" as an open transition word without precluding any additional or other elements.

It should also be noted that there are many alternative ways of implementing the methods and apparatuses of the disclosed aspects. It is therefore intended that the following appended claims be interpreted as including all such alterations, modifications, permutations, and substitute equivalents as fall within the true spirit and scope of the disclosed aspects.

What is claimed is:

1. A method for assessing quality of feedstock comprising:
    providing a sample containing a flour, wherein the flour is ground feedstock;
    contacting the sample containing the flour with a molecule that is detectibly altered by enzymatic activity of endogenous enzymes within the flour, wherein the enzymatic activity is esterase activity;
    detecting a total amount of enzymatically altered molecule by observing a change in fluorescence of the sample over a plurality of incubations; and
    correlating the detected total amount of enzymatically altered molecule to a quality value for the feedstock for ethanol production.

2. The method of claim 1, wherein the contacting comprises contacting the sample with a molecule that includes at least one of fluorescein diacetate and difluorofluorescein.

3. The method of claim 1, wherein the detecting the total amount of enzymatically altered molecule is performed using a fluorometer.

4. The method according to claim 1, wherein a first incubation from the plurality of incubations lasts about one minute and a second incubation from the plurality of incubations lasts about two minutes.

5. A method for assessing quality of feedstock by measuring a change in fluorescence over a plurality of incubations to determine levels of endogenous enzymes in the feedstock, the method comprising:
    grinding the feedstock to a flour;
    buffering the flour with a buffering solution to generate a buffered flour solution;
    combining a test solution to the buffered flour solution to generate a sample solution, wherein the test solution is detectibly altered by esterase activity;
    incubating the sample solution for a first time period;

measuring a first fluorescence value of the sample solution;
incubating the sample solution for a second time period;
measuring a second fluorescence value of the sample solution;
detecting a total amount of esterase activity by observing a change in fluorescence of the sample over the first time period and second time period; and
correlating the detected total amount of esterase activity to a quality value for the feedstock for ethanol production.

6. The method of claim 5, further comprising diluting the flour after grinding.

7. The method of claim 6, wherein diluting the flour comprises combining about 0.5 grams of flour with about 10 milliliters of water.

8. The method of claim 5, wherein the grinding comprises grinding feedstock that includes corn kernels.

9. The method of claim 5, wherein the grinding includes generating flour with greater than 90% fines.

10. The method of claim 5, wherein the buffering comprises buffering the flour with a phosphate buffered solution.

11. The method of claim 5, wherein the combining comprises combining to the buffered flour solution the test solution that includes fluorescein diacetate.

12. The method of claim 11, wherein the test solution includes fluorescein diacetate in acetone in a concentration of about 30 milligrams of fluorescein diacetate in 10 milliliters of acetone.

13. The method of claim 5, wherein the incubating includes incubating at approximately 30 degrees Celsius.

14. The method of claim 5, wherein first time period is for about one minute.

15. The method of claim 5, further comprising assigning a quality designation to the feedstock based upon a fluorescence index.

16. The method of claim 5, further comprising:
generating a fluorescence index by taking a difference between the second fluorescence value and the first fluorescence value.

17. The method of claim 16, wherein the second time period for about two minutes.

18. The method of claim 16, wherein measuring the first fluorescence value and the second fluorescence value includes using a fluorometer for emitting an excitation wavelength of about 494 nm and detecting an emission wavelength of about 521 nm.

* * * * *